United States Patent
Luo et al.

(10) Patent No.: US 12,424,336 B2
(45) Date of Patent: Sep. 23, 2025

(54) METHOD, DEVICE AND SYSTEM FOR TRACKING POTENTIAL INFECTED PERSONS IN PUBLIC PLACE DURING EPIDEMIC PERIOD

(71) Applicant: THE SECOND RESEARCH INSTITUTE OF CAAC, Chengdu (CN)

(72) Inventors: Qian Luo, Chengdu (CN); Wanli Dang, Chengdu (CN); Xiao Luo, Chengdu (CN); Rui Deng, Chengdu (CN); Long Geng, Chengdu (CN); Ye Pan, Chengdu (CN); Zaoxin Chen, Chengdu (CN); Ergai Yu, Chengdu (CN)

(73) Assignee: THE SECOND RESEARCH INSTITUTE OF CAAC, Chengdu (CN)

( * ) Notice: Subject to any disclaimer, the term of this patent is extended or adjusted under 35 U.S.C. 154(b) by 370 days.

(21) Appl. No.: 17/979,782

(22) Filed: Nov. 3, 2022

(65) Prior Publication Data
US 2023/0121997 A1 Apr. 20, 2023

Related U.S. Application Data

(63) Continuation of application No. PCT/CN2020/080855, filed on Mar. 24, 2020.

(30) Foreign Application Priority Data

Mar. 9, 2020 (CN) .......................... 202010154976.X (51) Int. Cl.
*G16H 50/80* (2018.01)
*G06V 20/52* (2022.01)

(52) U.S. Cl.
CPC ............ *G16H 50/80* (2018.01); *G06V 20/52* (2022.01)

(58) Field of Classification Search
None
See application file for complete search history.

(56) References Cited

U.S. PATENT DOCUMENTS

| 7,447,333 B1 * | 11/2008 | Masticola | G16H 50/80 |
| | | | 382/128 |
| 2013/0318027 A1 * | 11/2013 | Almogy | G16H 50/20 |
| | | | 706/52 |

(Continued)

FOREIGN PATENT DOCUMENTS

| CN | 103259962 A | 8/2013 |
| CN | 103310013 A | 9/2013 |

(Continued)

OTHER PUBLICATIONS

International Search Report issued in corresponding International application No. PCT/CN2020/080855, mailed Dec. 3, 2020.

(Continued)

*Primary Examiner* — Randolph I Chu (57) ABSTRACT

Disclosed are a method, device and system for tracking potential infected persons in a public place during an epidemic period. The method comprises: determining, according to associated information of a confirmed case, times of motions of the confirmed case in a public place and matching location information; searching for potential infected persons by means of video frame data provided by video monitoring devices in the public place based on an epidemic propagation mechanism; and tracking the potential infected persons based on multi-target tracking, and verifying the identity of the potential infected persons according to critical time nodes in the public place.

18 Claims, 6 Drawing Sheets

Determine, according to associated information of a confirmed case, time nodes of motions of the confirmed case in a public place and location information matching the time nodes — S110

Search for, according to the time nodes and location information of the confirmed case in the public place, potential infected persons by means of video frame data provided by video monitoring devices in the public place based on an epidemic propagation mechanism — S120

Track the potential infected persons based on multi-target tracking, and verify the identity of the potential infected persons according to time nodes of motions of the potential infected persons in the public place — S130

(56) References Cited

U.S. PATENT DOCUMENTS

| | | | | |
|---|---|---|---|---|
| 2017/0352119 A1* | 12/2017 | Pittman | | G16H 50/80 |
| 2018/0218463 A1* | 8/2018 | Jobling | | G06Q 10/025 |
| 2019/0252078 A1* | 8/2019 | Schubert | | G06N 3/044 |
| 2019/0356538 A1* | 11/2019 | Stanciu | | H04L 41/0843 |
| 2020/0388287 A1* | 12/2020 | Anushiravani | | G16H 20/10 |
| 2023/0152652 A1* | 5/2023 | Trikha | | H10K 59/65 |
| | | | | 700/276 |
| 2025/0025107 A1* | 1/2025 | Lee | | A61B 5/7282 |

FOREIGN PATENT DOCUMENTS

| | | | |
|---|---|---|---|
| CN | 105740615 A | | 7/2016 |
| CN | 109360660 A | * | 2/2019 |

OTHER PUBLICATIONS

Written Opinion of the International Searching Authority for No. PCT/CN2020/080855.

* cited by examiner

METHOD, DEVICE AND SYSTEM FOR TRACKING POTENTIAL INFECTED PERSONS IN PUBLIC PLACE DURING EPIDEMIC PERIOD

BACKGROUND OF THE INVENTION

1. Technical Field

The invention relates to the technical field of target tracking in heavily populated public places, in particular to a method, device and system for tracking potential infected persons in a public place during an epidemic period.

2. Description of Related Art

During the epidemic propagation process, assume there are three types of persons, namely person A, person B and person C, person C has been definitely come into contact with person A, so when person A is diagnosed as a patient, it is easy to determine that person C in contact with person A is also a patient. Assume person A encounters unacquainted person B in a public place (such as an airport, a bus station or a harbor during a trip), person A does not know the existence of person B, and person B does not know the existence of person A either. If it is found, after several days of virus incubation, that person A is virus-infected, person B who has been in contact with person A in the public place will be a potential virus-infected person who is highly dangerous because no one including himself/herself knows that he/she has been virus-infected before a definitive diagnosis. Person B may continue appear in public places without any protection, and virus spread and propagation within a wider range will be caused undoubtedly during the incubation period of person B if person B is certainly infected due to the contact with person A.

How to find potential infected persons (referred to as "person B") who once come into contact with a confirmed case or even a person from an epidemic focus (referred to as "person A") on a public vehicle or in a public place is an important part for epidemic control.

At present, there have already been some solutions or software for finding potential infected persons. For example, the following solutions may be adopted at the airport, in the waiting room or at the ticket entrance:

Solution 1: to check whether ourselves have ever been on the same flight with a confirmed case or our seat number is close to that of the confirmed case according to vehicle or flight information and seat information;

Solution 2: to analyze the probability of virus infection of a person based on travel data of travellers;

Solution 3: to actively find potential infected persons according to travel records of a confirmed case.

These three mainstream solutions have the following problems:

(1) Solution 1 can search for infected persons within a small range and can only locate the flight, and cannot locate and determine potential infected persons in the airport terminal where the confirmed case stays for a long time.

(2) Solution 2 actively searches for potential infected persons through association in time mainly based on the travel records of travellers and has a wide application range, but it has low analytical precision, checks and determines potential infected persons actively, and cannot passively screen out and search for potential infected persons and passive deletion and selection and verify the identity of the potential infected persons.

(3) According to Solution 3, persons who have come into contact with the confirmed case determine by themselves whether they are potentially infected according to released travel records of the confirmed case.

All these three solutions can find part of potential infected persons to some extent, but cannot determine the identity of potential infected persons at the airport terminal.

As can be seen, heavily populated public places where passengers stay for a long time, such as large airport terminals, train stations and bus stations, are primary focuses during epidemic defense. How to accurately locate potential infected persons in these public places according to the information of a confirmed case and verify the identity of the infected persons is a technical issue urgently to be settled by those skilled in the art.

BRIEF SUMMARY OF THE INVENTION

In view of this, the embodiments of the invention provides a method, device and system for tracking potential infected persons in a public place during an epidemic period, which determine the location and track of potential infected persons based on multi-target tracking using the epidemic propagation mechanism as an approach and verify the identity of the potential infected persons in terms of temporal and spatial dimension features.

In a first aspect, the invention discloses a method for tracking potential infected persons in a public place during an epidemic period, comprising:

Determining, according to associated information of a confirmed case, time nodes of motions of the confirmed case in a public place and location information matching the time nodes;

Searching for, according to the time nodes and location information of the confirmed case in the public place, potential infected persons by means of video frame data provided by video monitoring devices in the public place based on an epidemic propagation mechanism; and Tracking the potential infected persons based on multi-target tracking, and verifying the identity of the potential infected persons according to time nodes of motions of the potential infected persons in the public place.

Further, according to the method, the associated information of the confirmed case includes: identity information of the confirmed case and operation information of a vehicle taken by the confirmed case.

Further, according to the method, determining location information of the confirmed case in the public place comprises:

Determining corresponding video monitoring devices in the public places according to the corresponding time nodes of the motions of the confirmed case in the public place;

Receiving video frames at the time nodes extracted from the video monitoring devices; and Detecting, extracting and verifying the confirmed case in the video frames.

Further, according to the method, extracting and verifying the confirmed case in the video frames comprise:

Extracting locations and features of the confirmed case at different time nodes in different video frames to construct a feature space;

Constructing a spatial probability feature based on a moving distance and a track probability; and Determining a similarity of the confirmed case at adjacent time nodes in different video frames based on the feature space and the spatial probability feature; when the similarity is greater than a given threshold, continuing the tracking based on the confirmed case in the video frames to describe all locations of the confirmed case in the public place so as to verify a track of the confirmed case in the public place.

Further, according to the method, searching for potential infected persons by means of video frame data provided by video monitoring devices in the public place based on an epidemic propagation mechanism comprises:

Constructing, in the video frames, a circular area with the location of the confirmed case as a center and a distance of a given epidemic propagation range mapped into the video frames as a radius;

Determining pedestrians in the circular area as potential infected persons;

With a current video frame of the confirmed case as an initial video frame, performing forward and backward tracking from the time node corresponding to the initial video frame until the location of the confirmed case meets:

$$|O_i - O_{i-1}| = d_i$$

Where, $O_i$ represents a current location of the confirmed case, and $O_{i-1}$ represents another location of the confirmed case on the motion track;

Constructing a circular area with $O_i$ as the center and $d_i$ as the radius to search for potential infected persons again; and Repeating these steps until all infected persons in the public place are searched out.

Further, according to the method, tracking the potential infected persons based on multi-target tracking and verifying the identity of the potential infected persons comprise:

Extracting locations and features of a searched-out potential infected person at different time nodes in different video frames to construct a feature space;

Constructing a spatial probability feature based on a moving distance and a track probability;

Determining a similarity of the potential infected person at adjacent time nodes in different video frames based on the feature space and the spatial probability feature; when the similarity is greater than a given threshold, continuing the tracking based on the potential infected person in the video frames until it reaches a time node of registration of the potential infected person, and at this moment, verifying and reporting the identity of the potential infected person.

Further, after extracting locations and features of the confirmed case at different times in different video frames, the method further comprises: constructing a feature pyramid, and determining the feature space according to the feature pyramid; and After extracting locations and features of a searched-out potential infected person at different time in different video frames, the method also comprises: constructing a feature pyramid, and determining the feature space according to the feature pyramid.

Further, according to the method, determining a similarity of the confirmed case or the potential infected person at adjacent time nodes in different video frames based on the feature space and the spatial probability feature of the confirmed case or the potential infected person obtained based on the video frames comprises:

Letting the feature space constructed according to the feature pyramid extracted from the video frame at time i be $T_i = [T_{i1}, T_{i2}, T_{i3}]$;

Letting the feature space constructed according to the feature pyramid extracted from the video frame at time j=i+1 be $T_j = [T_{j1}, T_{j2}, T_{j3}]$;

Letting the spatial probability feature of the confirmed case or the potential infected person in different directions be $P_i$;

Calculating the similarity of the conformed case or the potential infected person in different video frames by:

$$Q_1 = P_i \cdot \frac{T_{i1} \cdot T_{j1}}{\|T_{i1}\| \cdot \|T_{j1}\|},$$

$$Q_2 = P_i \cdot \frac{T_{i2} \cdot T_{j2}}{\|T_{i2}\| \cdot \|T_{j2}\|},$$

$$Q_3 = P_i \cdot \frac{T_{i3} \cdot T_{j3}}{\|T_{i3}\| \cdot \|T_{j3}\|},$$

$$Q = P_1 \cdot Q_1 + P_2 \cdot Q_2 + P_3 \cdot Q_3 \; (P_1 + P_2 + P_3 = 1)$$

Where, Q is the similarity of the confirmed case or the potential infected person in different video frames, and i and j are both natural numbers, and in actual application, $P_1 > P_2 > P_3$.

In a second aspect, the invention further provides a device for tracking potential infected persons in a public place during an epidemic period, comprising:

A confirmed case search module used for determining, according to associated information of a confirmed case, time nodes of motions of the confirmed case in a public place and location information matching the time nodes;

A potential infected person search module used for searching for, according to the time nodes and location information of the confirmed case in the public place, potential infected persons by means of video frame data provided by video monitoring devices in the public place based on an epidemic propagation mechanism; and A potential infected person identity verification module used for tracking the potential infected persons based on multi-target tracking, and verifying the identity of the potential infected persons according to time nodes of motions of the potential infected persons in the public place.

Further, according to the device, the associated information of the confirmed case includes: identity information of the confirmed case and operation information of a vehicle taken by the confirmed case.

Further, according to the device, the confirmed case search module comprises:

A video monitoring device determining unit used for determining corresponding video monitoring devices in the public places according to the corresponding time nodes of the motions of the confirmed case in the public place;

A receiving unit used for receiving video frames at the time nodes extracted from the video monitoring devices; and A confirmed case determining module used for detecting, extracting and verifying the confirmed case in the video frames.

Further, according to the device, in the video frames, the confirmed case determining module further comprises:

A first feature space construction sub-unit used for extracting locations and features of the confirmed case at different time nodes in different video frames to construct a feature space;

A first space probability feature construction sub-unit used for constructing a spatial probability feature based on a moving distance and a track probability; and A first verification unit used for determining a similarity of the confirmed case at adjacent time nodes in different video frames based on the feature space and the spatial probability feature, continuing, when the similarity is greater than a given threshold, the tracking based on the confirmed case in the video frames until it reaches a time node of registration of the confirmed case, and verifying the confirmed case.

Further, according to the device, the potential infected person search module is used for:

Constructing, in the video frames, a circular area with the location of the confirmed case as a center and a distance of a given epidemic propagation range mapped into the video frames as a radius;

Determining pedestrians in the circular area as potential infected persons;

With a current video frame of the confirmed case as an initial video frame, performing forward and backward tracking from the time node corresponding to the initial video frame until the location of the confirmed case meets:

$$|O_i - O_{i-1}| = d_i$$

Where, $O_i$ represents a current location of the confirmed case, and $O_{i-1}$ represents another location of the confirmed case on the motion track; and Constructing a circular area with $O_i$ as the center and $d_i$ as the radius to search for potential infected persons again.

Further, according to the device, the potential infected person identity verification module comprises:

A second feature space construction sub-unit used for extracting locations and features of a searched-out potential infected person at different time nodes in different video frames to construct a feature space;

A second space probability feature construction sub-unit used for constructing a spatial probability feature based on a moving distance and a track probability;

A second verification sub-unit used for determining a similarity of the potential infected person at adjacent time nodes in different video frames based on the feature space and the spatial probability feature, continuing, when the similarity is greater than a given threshold, the tracking based on the potential infected person in the video frames until it reaches a time node of registration of the potential infected person, and verifying and reporting the identity of the potential infected person.

Further, after extracting locations and features of the confirmed case at different times in different video frames, the device further comprises: constructing a feature pyramid, and determining the feature space according to the feature pyramid; and after extracting locations and features of a searched-out potential infected person at different time in different video frames, the device also comprises: constructing a feature pyramid, and determining the feature space according to the feature pyramid.

Further, according to the device, the first verification sub-unit and the second verification sub-unit are used for:

Letting the feature space constructed according to the feature pyramid extracted from the video frame at time i be $T_i = [T_{i1}, T_{i2}, T_{i3},]$;

Letting the feature space constructed according to the feature pyramid extracted from the video frame at time j=i+1 be $T_j = [T_{j1}, T_{j2}, T_{j3}]$;

Letting the spatial probability feature of the confirmed case or the potential infected person in different directions be $P_i$;

Calculating the similarity of the conformed case or the potential infected person in different video frames by:

$$Q_1 = P_i \cdot \frac{T_{i1} \cdot T_{j1}}{\|T_{i1}\| \cdot \|T_{j1}\|},$$

$$Q_2 = P_i \cdot \frac{T_{i2} \cdot T_{j2}}{\|T_{i2}\| \cdot \|T_{j2}\|},$$

$$Q_3 = P_i \cdot \frac{T_{i3} \cdot T_{j3}}{\|T_{i3}\| \cdot \|T_{j3}\|},$$

$$Q = P_1 \cdot Q_1 + P_2 \cdot Q_2 + P_3 \cdot Q_3 \ (P_1 + P_2 + P_3 = 1)$$

Where, Q is the similarity of the confirmed case or the potential infected person in different video frames, and i and j are both natural numbers, and in actual application, $P_1 > P_2 > P_3$.

In a third aspect, the invention further discloses a method for tracking potential infected persons in a public place during an epidemic period. With an airport terminal as the public place, the method comprises: dividing the airport terminal into a check-in area, a security check area and a waiting area; performing the method for tracking potential infected persons in a public place during an epidemic period in the check-in area, the security check area and the waiting area; based on a confirmed case, obtaining a first set of potential infected persons in the check-in area, obtaining a second set of potential infected persons in the safety check area, and obtaining a third set of potential infected persons in the waiting area; and taking a union set of the first set, the second set and the third set as potential infected persons.

According to the invention, based on the existing monitoring environment of a public place (such as an airport terminal), potential infected persons associated with a confirmed case are actively searched in the public place under the precondition that the identity of the confirmed case is verified, and the identity of the potential infected persons is verified. Upon data testing, the precision of the invention can be over 80%, the issue of searching for and verifying potential infected persons in the public place is settled to a great extent, and the invention plays an important role in epidemic control.

BRIEF DESCRIPTION OF THE SEVERAL VIEWS OF THE DRAWINGS

To more clearly explain the technical solutions of the embodiments of the invention, drawings used for explaining the embodiments will be briefly introduced below. Obviously, the drawings in the following description are merely for some embodiments of the invention. Those ordinarily skilled in the art can obtain other drawings according to the following ones without creative labor.

DETAILED DESCRIPTION OF THE INVENTION

The embodiments of the invention will be described in detail below in conjunction with the accompanying drawings.

The implementation of the disclosure will be explained in conjunction with specific embodiments, and those skilled in the art can easily understand other advantages and effects of the disclosure with reference to the contents disclosed in this specification. Obviously, the embodiments in the following description are merely illustrative ones, and not all possible ones of the disclosure. The disclosure can be implemented or applied in other different forms, and all details in this specification can be modified or changed based on different ideas and applications without departing from the spirit of the invention. It should be noted that the following embodiments and features in the following embodiments can be combined without any conflict. All other embodiments obtained by those ordinarily skilled in the art without creative labor should fall within the protection scope of the disclosure.

It should be noted that all aspects of the embodiments within the scope of the appended claims are described below. Obviously, these aspects described in this specification can be reflected in different forms, and any specific structures and/or functions described in this specification are merely illustrative. Based on the disclosure, those skilled in the art should understand that any one aspect in this specification may be implemented independent of other aspects, and two or more of these aspects can be combined in various forms. For example, the device and/or method can be implemented using any number of these aspects expounded in this specification. In addition, the device and/method can be implemented using one or more other aspects expect those expounded in this specification.

It should also be noted that the figures in the following embodiments are used to illustratively explain the basic concept of the disclosure, and are not drawn according to the actual number, shape and size of components involved in the disclosure. During actual implementation, the shape, number and scale of the components can be changed, and the layout of the components may be more complicated.

In addition, for the sake of a thorough understanding of examples specific details are provided in the following description. However, those skilled in the art should understand that the aspects of the disclosure can be implemented without these specific details.

Before the steps of the solutions are described, "person B" will be defined.

During the epidemic propagation process, assume there are three types of persons, namely person A, person B and person C, person A is a confirmed virus-infected person, and before being confirmed as a virus-infected person, person A may come in contract with two types of persons, namely person B and person C; person A does not know person B and knows person C, so when person A is confirmed as a virus-infected person, it is easy to determine that person C is also virus-infected, but it is difficult to find person B because person A encounters unacquainted person B in a public place, person A does not know the existence of person B, and person B does not know the existence of person A either. So, person B is the biggest hidden trouble and cannot be found easily because no one knows who is person B and even person B himself/herself knows whether he/she is virus-infected.

One embodiment of the invention provides a method and system for tracking potential infected persons in a public place during an epidemic period, which determine the location and track of potential infected persons based on multi-target tracking using the epidemic propagation mechanism as an approach and verify the identity of the potential infected persons in terms of temporal and spatial dimension features. The method for tracking potential infected persons in a public place during an epidemic period comprises the following steps:

(1) Describing the location of a confirmed case in critical areas in conjunction with a business process of a public place;
(2) Searching and determining potential infected persons based on an epidemic propagation mechanism according to the location of the confirmed case; and
(3) Describing the track of the potential infected persons based on multi-target tracking, and verifying the identity of the potential infected persons.

Figure 1:
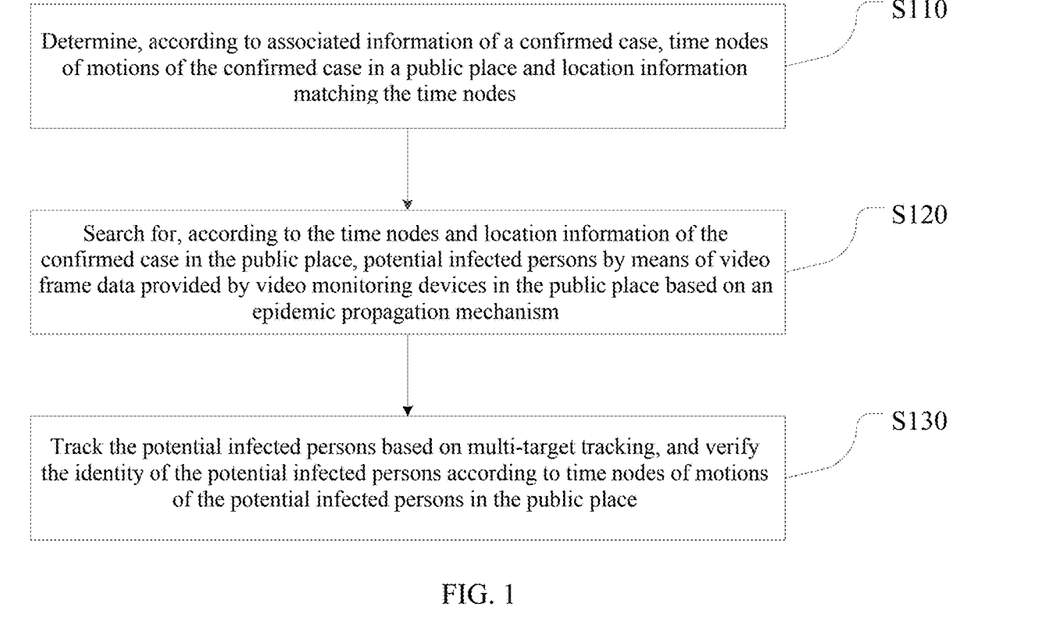
FIG. 1 illustrates a flow diagram of the steps of a method for tracking potential infected persons in a public place during an epidemic period according to one embodiment of the invention.

Referring to FIG. 1 which illustrates a flow diagram of the steps of the method for tracking potential infected persons in a public place during an epidemic period in this embodiment of the invention, the method comprises the following steps:

S110, time nodes of motions of a confirmed case in a public place and location information matching the time nodes are determined according to associated information of the confirmed case;

S120, according to the time nodes and location information of the confirmed case in the public place, potential infected persons are searched by means of video frame data provided by video monitoring devices in the public place based on an epidemic propagation mechanism; and S130, the potential infected persons are tracked based on multi-target tracking, and the identity of the potential infected persons is verified according to time nodes of motions of the potential infected persons in the public place.

Below, the method for tracking potential infected persons in a public place during an epidemic period will be explained in further detail with an airport terminal as an example. It should be noted that, although this embodiment is explained with the airport terminal as an example, the invention is not limited to the airport terminal and can be applied to other public places where video monitoring devices are available and identity verification is needed such as bus stations, train stations and harbors.

Figure 2:
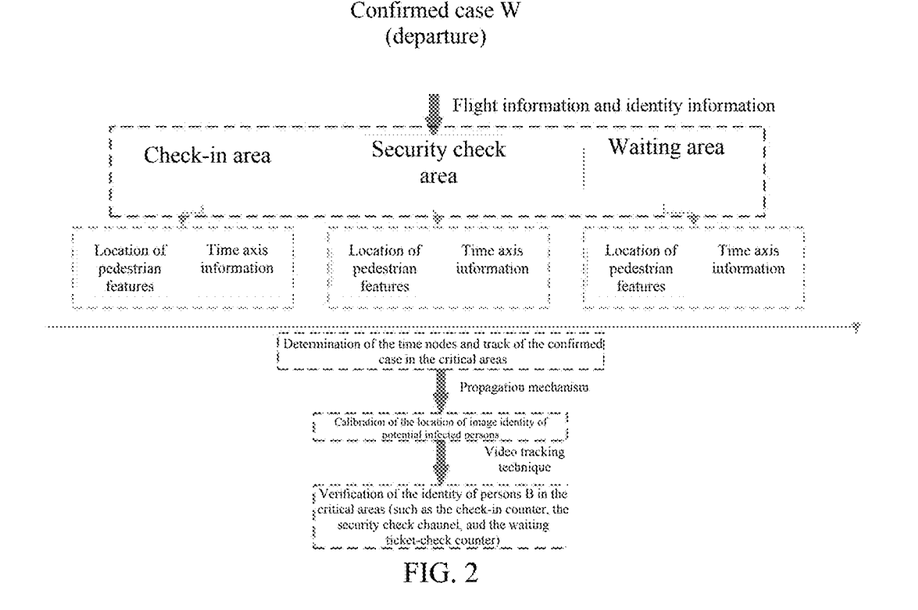
FIG. 2 illustrates a business flow diagram of the method for tracking potential infected persons in a public place during an epidemic period according to one embodiment of the invention.

Refer to FIG. 2 which illustrates a business flow diagram of the method for tracking potential infected persons in a public place during an epidemic period in this embodiment of the invention.

Figure 3:
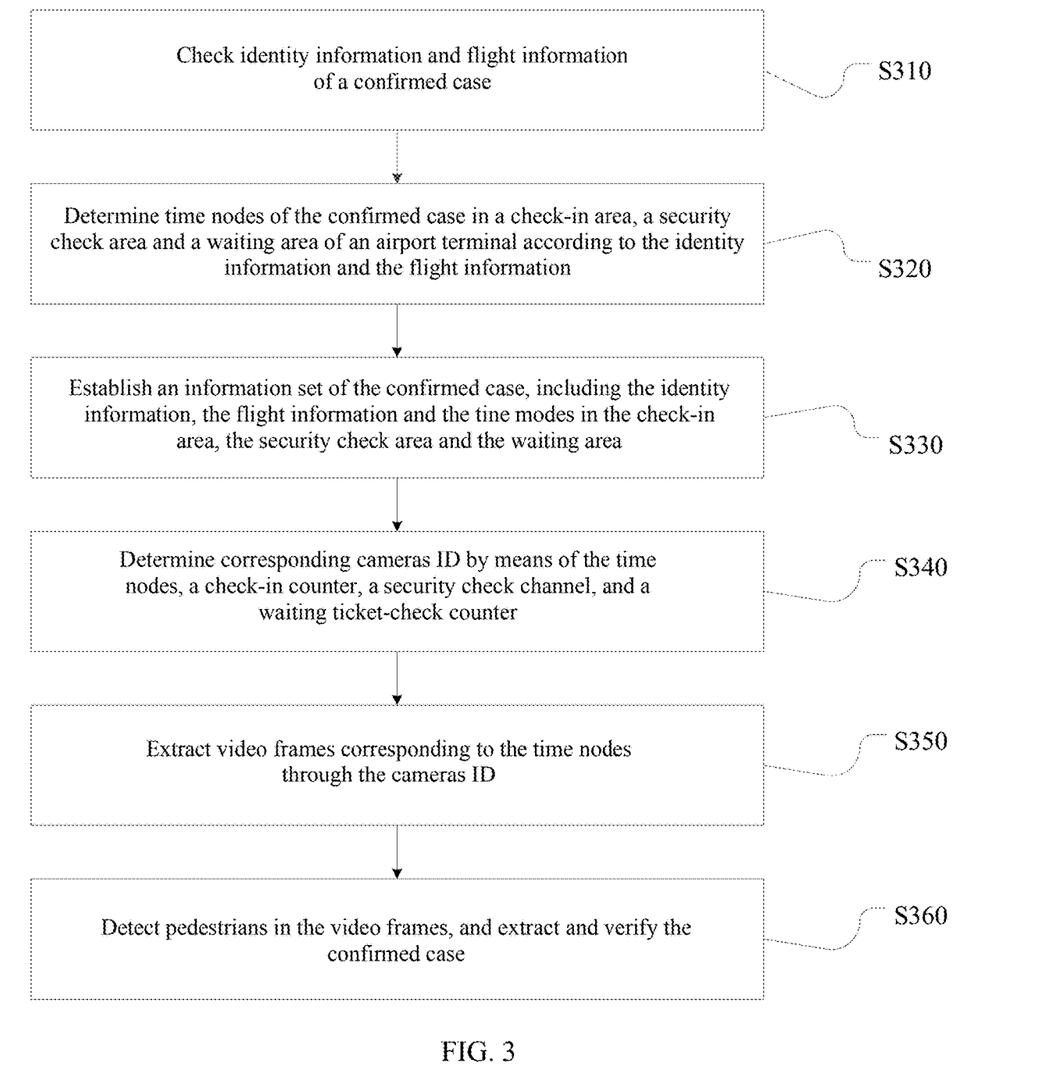
FIG. 3 illustrates a flow diagram of the step of determining time nodes of motions of a confirmed case in an airport terminal and location information matching the time nodes of the method for tracking potential infected persons in a public place during an epidemic period according to one embodiment of the invention.

In brief, before the departure of a confirmed virus-infected case, according to associated information of the confirmed case (including personal information of the confirmed case and operation information of a flight taken by the confirmed case), pedestrian features are located in a check-in area, a security check area and a waiting area based on an epidemic propagation mechanism in terms of time axis information of video frames to search for potential infected persons, wherein each area comprises three key points: (1) determination of time nodes and location information of the confirmed case in the critical areas; (2) calibration of the location and image identity of potential infected persons based on the virus propagation mechanism; and (3) tracking and verification of identity information of potential infected persons in the critical areas. In one embodiment, as shown in FIG. 3, this process comprises the following steps:

FIG. 3 illustrates how to the time nodes of motions of the confirmed case in a public place, and the location information matching the time nodes according to the associated information of the confirmed case, that is, how to determine the location of the confirmed virus-infected case in the critical areas.

Step 310, identity information and flight information of the confirmed case are checked;

Step S320, time nodes of the confirmed case in the check-in area, the security check area and the waiting area of the airport terminal are determined according to the identity information and the flight information;

Step S330, an information set A={Face, Fli, Time} of the confirmed case is established, wherein Face, as an expression of the identity information, refers to face information, Fli refers to the flight information, Time represents a set of time series, including a check-in time $C_{time}$, a security check time $S_{time}$ and a boarding ticket-check time $B_{time}$ of A, and is specifically expressed as:

Time={$C_{time}$, $S_{time}$, $B_{time}$}

Step S340, corresponding cameras ID are determined by means of the time nodes, a check-in counter, a security check channel, and a waiting ticket-check counter;

Step S350, video frames corresponding to the time nodes Time are extracted through the cameras ID; and Step S360, pedestrians in the video frames are detected, and the confirmed virus-infected case is extracted. This step may be implemented as follows:

Locations and features of the confirmed case at different time nodes in different video frames are extracted to construct a feature space;

A space probability feature is constructed based on a moving distance and a track probability; and The similarity of the confirmed case at adjacent time nodes in different video frames is determined based on the feature space and the space probability feature; when the similarity is greater than a given threshold, tracking continues based on the confirmed case in the video frames until it reaches a time node of registration of the confirmed case, and at this moment, the confirmed case is verified.

The verification method will be further described below in the case of potential infected persons (person B) and will not be detailed here. Please refer to the following description for the verification method.

Figure 4:
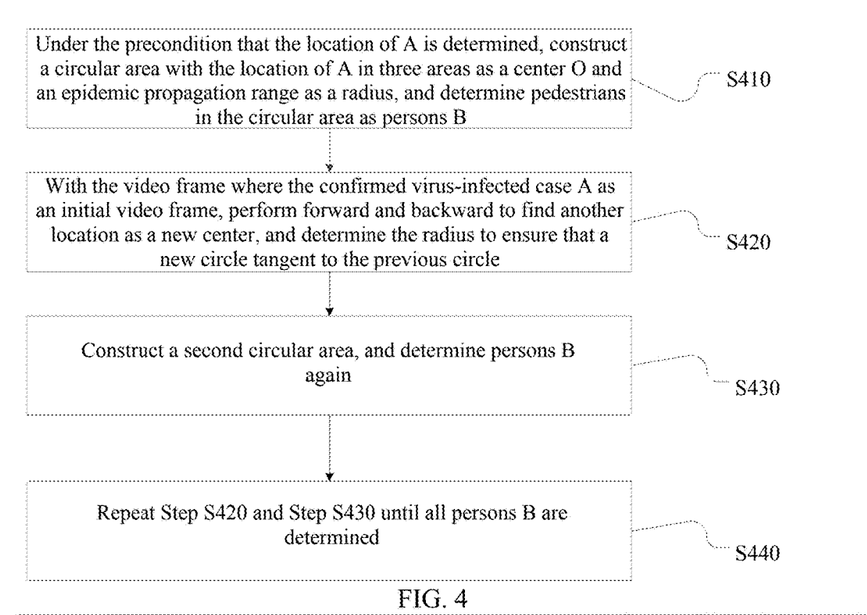
FIG. 4 illustrates a flow diagram of the step of searching for potential infected persons of the method for tracking potential infected persons in a public place during an epidemic period according to one embodiment of the invention.

Step S120, that is, how to search for potential infected persons according to the time nodes and location information of the confirmed case in the public place by means of video frame data provided by video monitoring devices in the public place based on an epidemic propagation mechanism will be described below. Specifically, referring to FIG. 4, Step S120 comprises the following steps:

Step S410, under the precondition that the location of the confirmed virus-infected case A is determined, a circular area is constructed with the location of A in the three areas as a center O and a distance of a given epidemic propagation range mapped into the video frames as a radius, and pedestrians in the circular area are determined as persons B (potential infected persons), the location of the persons B at this moment is marked as $B_i$, and the time of the video frames where the persons B are located is marked as $B_i^{time}$.

Step S420, with the video frame where the confirmed virus-infected case A is located as an initial video frame, forward and backward tracking is performed from the time $C_{time}$, $S_{time}$, $B_{time}$ of A in the three areas until the location $O_i$ of A meets the following relation:

$$|O_i - O_{i-1}| = d_i =$$

Where, $d_i$ represents the distance of an actual epidemic propagation distance mapped into the video frames;

Step S430, a circular area is constructed with $O_i$ as the center and $d_i$ as the radius to determine persons B $B_j$;

Step S440, the first step and the second step are repeated until all persons B are determined.

Below, Step S130 will be further explained. In one embodiment, the potential infected persons are tracked and the identity of the potential infected persons is verified through the following steps:

i, with the extracted video frame corresponding to the time node $B_i^{time}$ as an initial frame, the location and features of $B_i$ are determined;

ii, a feature pyramid of $B_i$ in this video frame is extracted and constructed to form a feature space;

iii, a space probability feature, mainly including a moving distance and a track probability, is constructed to track $B_i$; and iv, $B_i$ is tracked until $B_i$ reaches the check-in counter, the security check channel or the waiting ticket-check counter, and identity information of persons B is verified according to the corresponding time node.

In this embodiment, potential infected persons associated with the confirmed case in the public place are searched actively based on an existing monitoring environment of the airport terminal under the precondition that the identity of the confirmed case is verified, and the identity of the potential infected persons is determined. Upon data tests, the precision of the method can be over 80%, the issue of searching for and verifying potential infected persons in a public traffic place is settled to a great extent, and the method plays an important role in epidemic control.

The method for tracking potential infected persons in a public place during an epidemic period will be explained below in conjunction with a more specific embodiment. In this embodiment, the method will be explained with the security check area of the airport terminal as an example.

Step 1: a time node of the motion of a confirmed case A in the airport terminal, and location information matching the time node are determined according to associated information of the confirmed case A.

Specifically, the location and time of the confirmed case A appearing in the security check channel are determined according to identify information and flight information of the confirmed case A, wherein the ticket-check time of the confirmed case A in the ticket-check area at an airport is set as 11:23, and the number of the security check channel is 10.

Figure 5:
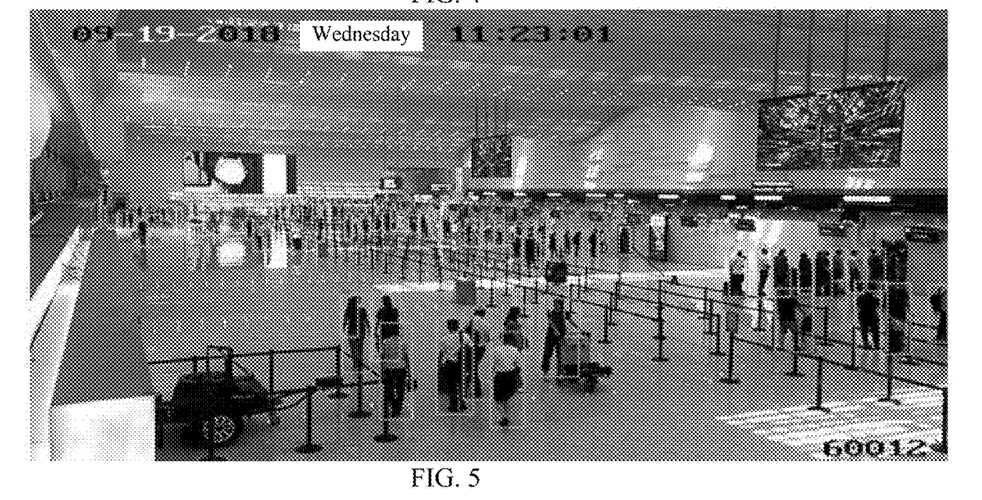
FIG. 5 illustrates a schematic diagram of the step of detecting and numbering pedestrians in video frames where the confirmed case is located of the method for tracking potential infected persons in a public place during an epidemic period according to one embodiment of the invention.

Video frames are extracted according to the time node 11:23 and the security check channel 10, and one frame of image is acquired from the video frames. Then, this frame of image is blocked, and pedestrians are detected through an RCNN model in the prior art, and are numbered, as shown in FIG. 5. According to the ticket-check location, it is determined that the number of the confirmed case A in the image is 45, and the box marked with A in FIG. 5 is the confirmed case A.

Step 2: according to the time node and location information of the confirmed case A in the security check area of the airport terminal, potential infected persons, namely persons B, are searched by means of video frame data provided by video monitoring devices in the security check area of the airport terminal based on an epidemic propagation mechanism.

According to the epidemic propagation mechanism, all persons within a range of m meters and staying for time t can be determined as potential infected persons B.

A security distance between pedestrians at the ticket-check counter in the security check area is d, and the distance of the security distance mapped into the image is y, which is defined as a reference distance based on which a radius will be calculated later;

According to a video perspective model, a proportional relation between distance changes in a three-dimensional space and distance changes in a two-dimensional space is $$\frac{y}{d} = a.$$

The location of the confirmed case in the image is determined, wherein the size of m mapped into the image is ma.

Figure 6:
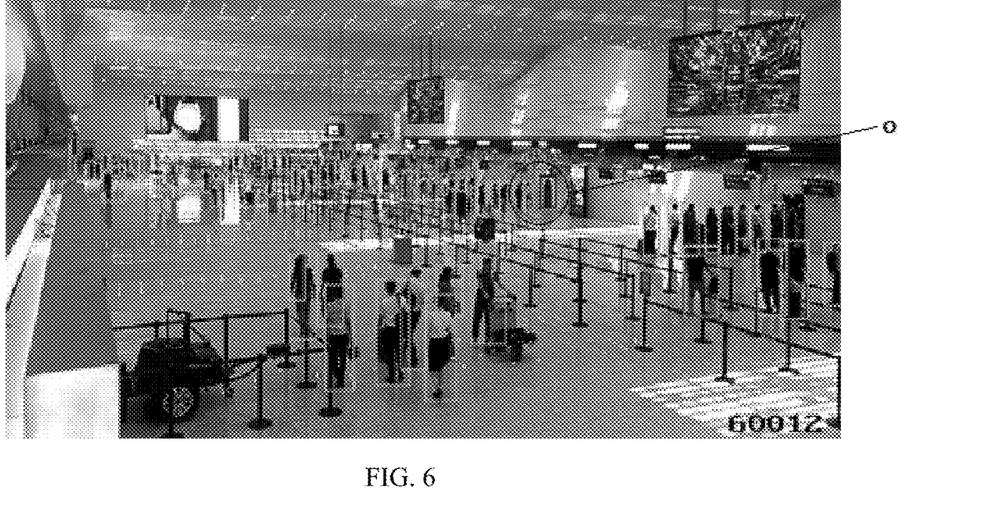
FIG. 6 illustrates a schematic diagram of the step of constructing a planar circle with the confirmed case as a center to determine a first batch of potential infected persons of the method for tracking potential infected persons in a public place during an epidemic period according to one embodiment of the invention.

In the video frames, a circle with the location of the confirmed case A as the center and ma as the radius is constructed, as shown in FIG. 6. FIG. 6 illustrates a first batch of potential infected persons determined in a planar circle constructed with the confirmed case as the center. Where, m=1 m, and a=0.05. In FIG. 6, persons in circle O is the first batch of potential infected persons $B_1$ searched out, and the potential infected persons $B_1$ are numbered as 19 and 30 respectively.

Figure 7:
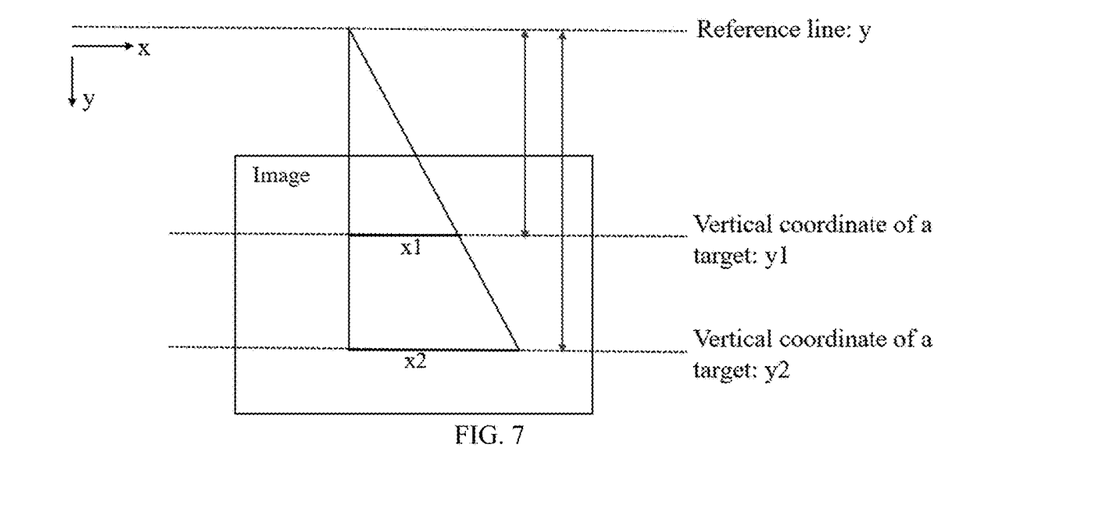
FIG. 7 illustrates a schematic diagram of a model for calculating the radius of circle $O_1$ of the method for tracking potential infected persons in a public place during an epidemic period according to one embodiment of the invention.

Next, the confirmed case A is tracked backward from current location by means of historical data, and circle $O_1$ is constructed with a previous location of the confirmed case A as the center, wherein circle O is tangent to circle $O_1$, and the radius of circle $O_1$ is calculated based on the model shown in FIG. 7.

In FIG. 7, $y_1$ represents the location of the confirmed case in circle $O_1$ and a y-axis value of a corresponding two-dimensional coordinate system, $x_1$ represents an X-axis value of the location of the confirmed case in circle $O_1$, the coordinate of a reference line of the confirmed case is (x, y), $y_2$ and $x_2$ represent the location of the confirmed case in circle O, and pixels (areas) $S_1$ and $S_2$ of $y_2$ and $x_2$ in the image meets the following relation:

$$S_2 = S_1 \cdot \frac{y_2 - y}{y_1 - y} \cdot \frac{x_2 - x}{x_1 - x}$$

Assume the radius of $O_1$ is $r_1$ and the radius of O is r, the formula for calculating $r_1$ is:

$$r_1 = r \cdot \frac{S_1}{S_2} = r \cdot \frac{y_1 - y}{y_2 - y} \cdot \frac{x_1 - x}{x_2 - x} = ma \cdot \frac{y_1 - y}{y_2 - y} \cdot \frac{x_1 - x}{x_2 - x}$$

r and $r_1$ meet the following relation:

$$r + r_1 = ma + ma \cdot \frac{y_1 - y}{y_2 - y} \cdot \frac{x_1 - x}{x_2 - x}$$

Figure 8:
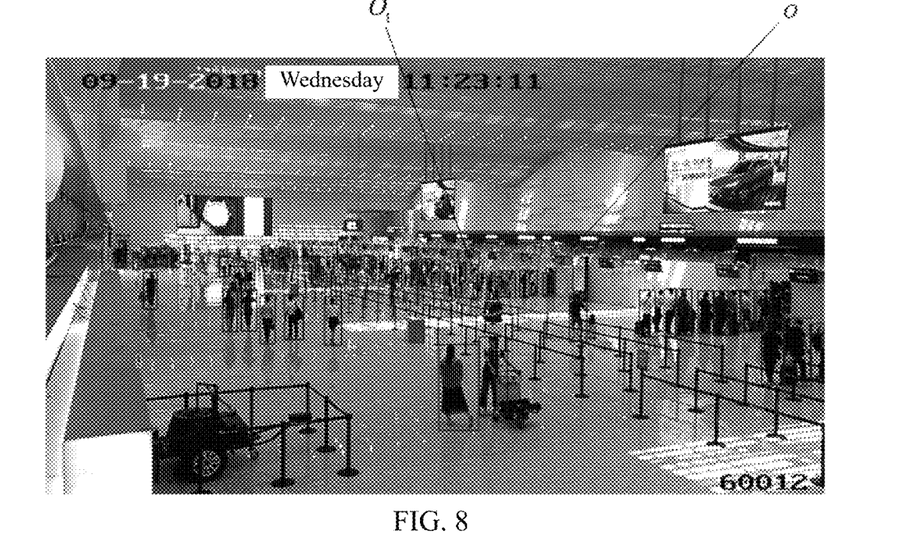
FIG. 8 illustrates a schematic diagram of a second batch of potential infected persons in circle $O_1$ externally tangent to circle O of the method for tracking potential infected persons in a public place during an epidemic period according to one embodiment of the invention.

Circle $O_1$ is determined as mentioned above, and then potential infected persons in circle $O_1$ are determined. Refer to FIG. 8 which illustrates a schematic diagram of a second batch of potential infected persons in circle $O_1$ tangent to circle O.

The process from circle O to circle $O_1$ is repeated until the location of all potential infected persons, namely persons B, is determined according to the motion track of the confirmed case A.

Step 3: the potential infected persons are tracked and the identity of the potential infected persons is verified. In this embodiment, the potential infected persons are tracked based on a multi-target tracking technique, and the identity of the potential infected persons is verified.

As mentioned above, the location of the infected persons, which are number as 19 and 30, respectively, in circle O have been determined. The tracking technique for potential infected persons is also suitable for the confirmed case.

Figure 9:
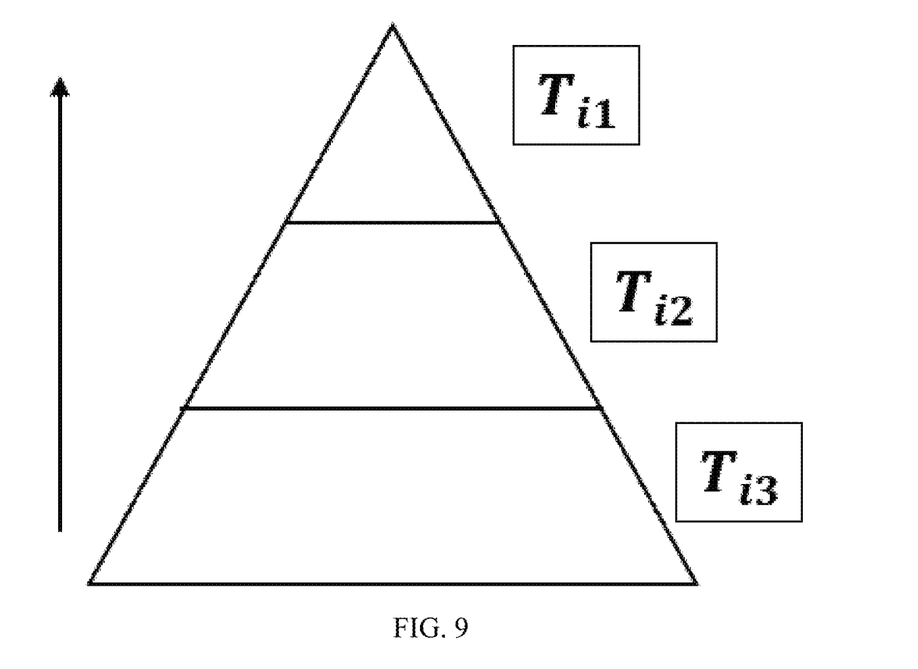
FIG. 9 illustrates a schematic diagram of a feature pyramid of the method for tracking potential infected persons in a public place during an epidemic period according to one embodiment of the invention.

The video frame matching $B_i^{time}$ is input to a mask-RCNN network in the prior art, features of pedestrians 19 and 30 are extracted, and a feature pyramid of the pedestrians 19 and 30 is constructed to construct a feature space. The use of the feature pyramid allows more advanced semantic information to be detected. The feature space is:

$$T_i = [T_{i1}, T_{i2}, T_{i3}]$$

Referring to FIG. 9 which is a schematic diagram of the feature pyramid. In FIG. 9, the semantic information of each layer becomes higher from bottom to top, the semantics becomes stronger, detected information becomes more advanced, and mined image information becomes deeper.

Pedestrians in the frame of image matching $B_i^{time}+1$ are detected, and a feature pyramid of the pedestrians is constructed and is marked as:

$$T_j=[T_{j1}, T_{j2}, T_{j3}]$$

According to the geographic location features of the security check area, the spatial motion direction of pedestrians is certain, and the probabilities of moving in different directions of the pedestrians are different and are set as $P_i$ ($P_i$ is a statistical empirical value, for example, at the security checkpoint, the probability of moving towards the security checkpoint of pedestrians is greater than the probability of moving in other directions). So, the similarity (Q) is defined as:

$$Q = P_i \cdot \frac{T_i \cdot T_j}{\|T_i\| \cdot \|T_j\|}$$

To reduce the calculation amount, features of the corresponding layer are used for calculating the similarity in an actual case as follows:

$$Q_1 = P_i \cdot \frac{T_{i1} \cdot T_{j1}}{\|T_{i1}\| \cdot \|T_{j1}\|},$$

$$Q_2 = P_i \cdot \frac{T_{i2} \cdot T_{j2}}{\|T_{i2}\| \cdot \|T_{j2}\|},$$

$$Q_3 = P_i \cdot \frac{T_{i3} \cdot T_{j3}}{\|T_{i3}\| \cdot \|T_{j3}\|},$$

Finally:

$$Q=P_1 \cdot Q_1+P_2 \cdot Q_2+P_3 \cdot Q_3 \ (P_1+P_2+P_3=1)$$

In actual application, $P_1>P_2>P_3$.

In this way, the redundancy of calculation based on all features is avoided, and the calculation speed in actual application is further increased.

The position of the potential infected persons in the frame matching $B_i^{time}+1$ is determined according to the similarity, and tracking continues until the location of the potential infected persons is the ticket-check counter near the security check channel, and the identity of the infected persons B is verified according to ticket check information and is reported.

In one embodiment, in Step 1, the identity of the confirmed case A in the security check area is determined based on the similarity and is checked continuously, and the algorithm adopted in Step 1 is the same as the algorithm mentioned here, and will not be detailed anymore.

It should be noted that, in this embodiment, how the identity of potential infected persons B in the security check area is verified is explained by way of an example, and potential infected persons B in the check-in area and the waiting area, which are not involved in this embodiment, can be verified in the same way, which will not be detailed here. During specific implementation, based on the confirmed case, a first set of potential infected persons is obtained in the check-in area, a second set of potential infected persons is obtained in the safety check area, a third set of potential infected persons is obtained in the waiting area; and a union set of the first set, the second set and the third set is taken as potential infected persons.

In this embodiment, based on the existing monitoring environment of a public place (such as an airport terminal), potential infected persons associated with a confirmed case are actively searched in the public place under the precondition that the identity of the confirmed case is verified, and the identity of the potential infected persons is verified. Upon data testing, the precision of the method in this embodiment can be over 80%, the issue of searching for and verifying potential infected persons in the public place is settled to a great extent, and the method in this embodiment plays an important role in epidemic control.

Figure 10:
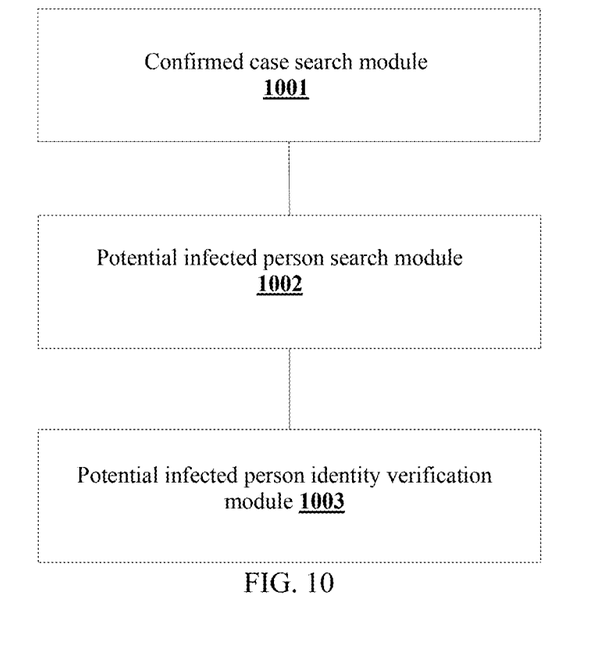
FIG. 10 is a structural block diagram of a device for tracking potential infected persons in a public place during an epidemic period according to one embodiment of the invention.

In a second aspect, the invention further provides a device for tracking potential infected persons in a public place during an epidemic period. As shown in FIG. 10, the device comprises:

A confirmed case search module 1001 used for determining, according to associated information of a confirmed case, time nodes of motions of the confirmed case in a public place and location information matching the time nodes;

A potential infected person search module 1002 used for searching for, according to the time nodes and location information of the confirmed case in the public place, potential infected persons by means of video frame data provided by video monitoring devices in the public place based on an epidemic propagation mechanism; and A potential infected person identity verification module 1003 used for tracking the potential infected persons based on multi-target tracking, and verifying the identity of the potential infected persons according to time nodes of motions of the potential infected persons in the public place.

It should be noted that the principle of the device for tracking potential infected persons in a public place during an epidemic period is the same as the principle of the method for tracking potential infected persons in a public place during an epidemic period, which has been explained above, and relevant details can be cross-referred, and will not be detailed here.

In addition, one embodiment of the invention further provides a system for tracking potential infected persons in a public place during an epidemic period, which comprises: at least one processor, and a memory in communication connection with the at least one processor, wherein an instruction to be executed by the at least one processor is stored in the memory, and when the instruction is executed by the at least one processor, the at least one processor implements the method for tracking potential infected persons in a public place during an epidemic period in the above embodiment.

The method for tracking potential infected persons in a public place during an epidemic period has been explained above, and relevant details can be cross-referred, and will not be detailed here.

The above embodiments are merely specific ones of the invention, and the protection scope of the invention is not limited to these embodiments. All variations or substitutions easily obtained by any skilled in the art within the technical scope of the invention should fall within the protection scope of the invention. Thus, the protection scope of the invention should be subjected to the protection scope of the claims.

What is claimed is:

1. A method for tracking potential infected persons in a public place during an epidemic period, wherein the method is executed by at least one processor, the method comprising:

receiving associated information of a confirmed case, wherein the associated information comprises identity information of the confirmed case and operation information of a vehicle taken by the confirmed case;

determining a public place where the vehicle is about to depart;

determining, by means of video frame data provided by video monitoring devices in the public place, time nodes of motions of the confirmed case in the public place and location information of the confirmed case matching the time nodes;

searching for, according to the time nodes and location information of the confirmed case in the public place, potential infected persons by means of the video frame data provided by the video monitoring devices in the public place based on an epidemic propagation mechanism; and tracking the potential infected persons based on multi-target tracking, and verifying the identity of the potential infected persons according to time nodes of motions of the potential infected persons in the public place;

wherein tracking the potential infected persons based on multi-target tracking and verifying the identity of the potential infected persons comprise:

extracting locations and features of a searched-out potential infected person at different time nodes in different video frames to construct a feature space;

constructing a spatial probability feature based on a moving distance and a track probability;

determining a similarity of the potential infected person at adjacent time nodes in different video frames based on the feature space and the spatial probability feature; when the similarity is greater than a given threshold, continuing the tracking based on the potential infected person in the video frames until it reaches a time node of registration of the potential infected person, and verifying and reporting the identity of the potential infected person.

2. The method for tracking potential infected persons in a public place during an epidemic period according to claim 1, wherein:

determining location information of the confirmed case in the public place comprises:

determining corresponding video monitoring devices in the public places according to the corresponding time nodes of the motions of the confirmed case in the public place;

receiving video frames at the time nodes extracted from the video monitoring devices; and detecting, extracting and continuously tracking and verifying the confirmed case in the video frames.

3. The method for tracking potential infected persons in a public place during an epidemic period according to claim 2, wherein detecting, extracting and continuously tracking and verifying the confirmed case in the video frames comprise:

extracting locations and features of the confirmed case at different time nodes in different video frames to construct a feature space;

constructing a spatial probability feature based on a moving distance and a track probability; and determining a similarity of the confirmed case at adjacent time nodes in different video frames based on the feature space and the spatial probability feature; when the similarity is greater than a given threshold, continuing the tracking based on the confirmed case in the video frames to describe all locations of the confirmed case in the public place so as to verify a track of the confirmed case in the public place.

4. The method for tracking potential infected persons in a public place during an epidemic period according to claim 3, wherein searching for potential infected persons by means of video frame data provided by video monitoring devices in the public place based on an epidemic propagation mechanism comprises:

constructing, in the video frames, a circular area with the location of the confirmed case as a center and a distance of a given epidemic propagation range mapped into the video frames as a radius;

determining pedestrians in the circular area as potential infected persons;

with a current video frame of the confirmed case as an initial video frame, performing forward and backward tracking from the time node corresponding to the initial video frame until the location of the confirmed case meets:

$$|O_i - O_{i-1}| = d_i$$

where, $O_i$ represents a current location of the confirmed case, and $O_{i-1}$ represents another location of the confirmed case on the motion track;

constructing a circular area again with $O_i$ as the center and $d_i$ as the radius to search for potential infected persons again; and repeating these steps until all infected persons in the public place are searched out.

5. The method for tracking potential infected persons in a public place during an epidemic period according to claim 4, wherein:

after extracting locations and features of the confirmed case at different times in different video frames, the method further comprises: constructing a feature pyramid, and determining the feature space according to the feature pyramid; and after extracting locations and features of a searched-out potential infected person at different time in different video frames, the method also comprises: constructing a feature pyramid, and determining the feature space according to the feature pyramid.

6. The method for tracking potential infected persons in a public place during an epidemic period according to claim 5, wherein:

determining a similarity of the confirmed case or the potential infected person at adjacent time nodes in different video frames based on the feature space and the spatial probability feature of the confirmed case or the potential infected person obtained based on the video frames comprises:

letting the feature space constructed according to the feature pyramid extracted from the video frame at time i be $T_i = [T_{i1}, T_{i2}, T_{i3}]$;

letting the feature space constructed according to the feature pyramid extracted from the video frame at time j=i+1 be $T_j = [T_{j1}, T_{j2}, T_{j3}]$;

letting the spatial probability feature of the confirmed case or the potential infected person in different directions be $P_i$;

calculating the similarity of the conformed case or the potential infected person in different video frames by:

$$Q_1 = P_i \cdot \frac{T_{i1} \cdot T_{j1}}{\|T_{i1}\| \cdot \|T_{j1}\|},$$

$$Q_2 = P_i \cdot \frac{T_{i2} \cdot T_{j2}}{\|T_{i2}\| \cdot \|T_{j2}\|},$$

-continued $$Q_3 = P_i \cdot \frac{T_{i3} \cdot T_{j3}}{\|T_{i3}\| \cdot \|T_{j3}\|},$$

$Q=P_1 \cdot Q_1+P_2 \cdot Q_2+P_3 \cdot Q_3 (P_1+P_2+P_3=1)$ where, Q is the similarity of the confirmed case or the potential infected person in different video frames, and i and j are both natural numbers, and in actual application, $P_1>P_2>P_3$.

7. A method for tracking potential infected persons in a public place during an epidemic period, comprising:
with an airport terminal as the public place,
dividing the airport terminal into a check-in area, a security check area and a waiting area;
performing the method for tracking potential infected persons in a public place during an epidemic period according to claim 1 in the check-in area, the security check area and the waiting area;
based on a confirmed case, obtaining a first set of potential infected persons in the check-in area, obtaining a second set of potential infected persons in the safety check area, and obtaining a third set of potential infected persons in the waiting area; and
taking a union set of the first set, the second set and the third set as potential infected persons.

8. A method for tracking potential infected persons in a public place during an epidemic period, comprising:
with an airport terminal as the public place,
dividing the airport terminal into a check-in area, a security check area and a waiting area;
performing the method for tracking potential infected persons in a public place during an epidemic period according to claim 2 in the check-in area, the security check area and the waiting area;
based on a confirmed case, obtaining a first set of potential infected persons in the check-in area, obtaining a second set of potential infected persons in the safety check area, and obtaining a third set of potential infected persons in the waiting area; and
taking a union set of the first set, the second set and the third set as potential infected persons.

9. A method for tracking potential infected persons in a public place during an epidemic period, comprising:
with an airport terminal as the public place,
dividing the airport terminal into a check-in area, a security check area and a waiting area;
performing the method for tracking potential infected persons in a public place during an epidemic period according to claim 3 in the check-in area, the security check area and the waiting area;
based on a confirmed case, obtaining a first set of potential infected persons in the check-in area, obtaining a second set of potential infected persons in the safety check area, and obtaining a third set of potential infected persons in the waiting area; and
taking a union set of the first set, the second set and the third set as potential infected persons.

10. A method for tracking potential infected persons in a public place during an epidemic period, comprising:
with an airport terminal as the public place,
dividing the airport terminal into a check-in area, a security check area and a waiting area;
performing the method for tracking potential infected persons in a public place during an epidemic period according to claim 4 in the check-in area, the security check area and the waiting area;
based on a confirmed case, obtaining a first set of potential infected persons in the check-in area, obtaining a second set of potential infected persons in the safety check area, and obtaining a third set of potential infected persons in the waiting area; and
taking a union set of the first set, the second set and the third set as potential infected persons.

11. A method for tracking potential infected persons in a public place during an epidemic period, comprising:
with an airport terminal as the public place,
dividing the airport terminal into a check-in area, a security check area and a waiting area;
performing the method for tracking potential infected persons in a public place during an epidemic period according to claim 5 in the check-in area, the security check area and the waiting area;
based on a confirmed case, obtaining a first set of potential infected persons in the check-in area, obtaining a second set of potential infected persons in the safety check area, and obtaining a third set of potential infected persons in the waiting area; and
taking a union set of the first set, the second set and the third set as potential infected persons.

12. A method for tracking potential infected persons in a public place during an epidemic period, comprising:
with an airport terminal as the public place,
dividing the airport terminal into a check-in area, a security check area and a waiting area;
performing the method for tracking potential infected persons in a public place during an epidemic period according to claim 6 in the check-in area, the security check area and the waiting area;
based on a confirmed case, obtaining a first set of potential infected persons in the check-in area, obtaining a second set of potential infected persons in the safety check area, and obtaining a third set of potential infected persons in the waiting area; and
taking a union set of the first set, the second set and the third set as potential infected persons.

13. A device for tracking potential infected persons in a public place during an epidemic period, comprising:
a confirmed case search module used for receiving associated information of a confirmed case, determining a public place where the vehicle is about to depart, and determining time nodes of motions of the confirmed case in the public place and location information of the confirmed case matching the time nodes by video frame data provided by video monitoring devices in the public place;
a potential infected person search module used for searching for, according to the time nodes and location information of the confirmed case in the public place, potential infected persons by means of the video frame data provided by the video monitoring devices in the public place based on an epidemic propagation mechanism; and
a potential infected person identity verification module used for tracking the potential infected persons based on multi-target tracking, and verifying the identity of the potential infected persons according to time nodes of motions of the potential infected persons in the public place;
wherein the associated information comprises identity information of the confirmed case and operation information of a vehicle taken by the confirmed case;

wherein tracking the potential infected persons based on multi-target tracking and verifying the identity of the potential infected persons comprises:
extracting locations and features of a searched-out potential infected person at different time nodes in different video frames to construct a feature space;
constructing a spatial probability feature based on a moving distance and a track probability;
determining a similarity of the potential infected person at adjacent time nodes in different video frames based on the feature space and the spatial probability feature; when the similarity is greater than a given threshold, continuing the tracking based on the potential infected person in the video frames until it reaches a time node of registration of the potential infected person, and
verifying and reporting the identity of the potential infected person.

14. A system for tracking potential infected persons in a public place during an epidemic period, comprising:
the at least one processor; and
a memory in communication connection with the at least one processor; wherein:
an instruction to be executed by the at least one processor is stored in the memory; and when the instruction is executed by the at least one processor, the at least one processor implements the method for tracking potential infected persons in a public place during an epidemic period according to claim 1.

15. A system for tracking potential infected persons in a public place during an epidemic period, comprising:
the at least one processor; and
at least one processor; and
a memory in communication connection with the at least one processor; wherein:
an instruction to be executed by the at least one processor is stored in the memory; and when the instruction is executed by the at least one processor, the at least one processor implements the method for tracking potential infected persons in a public place during an epidemic period according to claim 2.

16. A system for tracking potential infected persons in a public place during an epidemic period, comprising:
the at least one processor; and
a memory in communication connection with the at least one processor; wherein:
an instruction to be executed by the at least one processor is stored in the memory; and when the instruction is executed by the at least one processor, the at least one processor implements the method for tracking potential infected persons in a public place during an epidemic period according to claim 3.

17. A system for tracking potential infected persons in a public place during an epidemic period, comprising:
the at least one processor; and
a memory in communication connection with the at least one processor; wherein:
an instruction to be executed by the at least one processor is stored in the memory; and when the instruction is executed by the at least one processor, the at least one processor implements the method for tracking potential infected persons in a public place during an epidemic period according to claim 4.

18. A system for tracking potential infected persons in a public place during an epidemic period, comprising:
the at least one processor; and
a memory in communication connection with the at least one processor; wherein:
an instruction to be executed by the at least one processor is stored in the memory; and when the instruction is executed by the at least one processor, the at least one processor implements the method for tracking potential infected persons in a public place during an epidemic period according to claim 6.

* * * * *